US00PP30333P3

(12) United States Plant Patent
Thomsen

(10) Patent No.: US PP30,333 P3
(45) Date of Patent: Apr. 2, 2019

(54) ***EUPHORBIA MILII* PLANT NAMED '12-01-ZEU'**

(50) Latin Name: ***Euphorbia milii* Desmoul.**
Varietal Denomination: 12-01-ZEU

(71) Applicant: Hjortebjerg Plant Licence A/S, Sonderso (DK)

(72) Inventor: Steen Thomsen, Sonderso (DK)

(73) Assignee: Hjortebjerg Plant Licence A/S, Sonderso (DK)

( * ) Notice: Subject to any disclaimer, the term of this patent is extended or adjusted under 35 U.S.C. 154(b) by 42 days.

(21) Appl. No.: 15/530,616

(22) Filed: Feb. 8, 2017

(65) Prior Publication Data

US 2017/0164538 P1 Jun. 8, 2017

Related U.S. Application Data

(63) Continuation of application No. 14/544,905, filed on Mar. 6, 2015, now abandoned.

(30) Foreign Application Priority Data

Mar. 7, 2014 (QZ) ..... PBR 201403293

(51) Int. Cl.
*A01H 5/02* (2018.01)

(52) U.S. Cl.
USPC ..... Plt./302

(58) Field of Classification Search
USPC ..... Plt./263.1, 302
See application file for complete search history.

*Primary Examiner* — Susan McCormick Ewoldt
*Assistant Examiner* — Karen M Redden
(74) *Attorney, Agent, or Firm* — Sheppard Mullin Richter & Hampton LLP

(57) ABSTRACT

A new and distinct cultivar of *Euphorbia milii* plant named '12-01-ZEU', particularly characterized by its medium plant height about 20-22 cm, and its width about 16-18 cm; upright to spreading, compact growth habit; grouped disposition of spines; leaves of medium length about 5-6 cm, and a width about 1.5-2 cm; with the color of the upper side being RHS Yellow-Green 147A (but darker), and the underside being RHS Grayed-Purple 177A; and upper side color of its colorful bracts being RHS Red 45D.

5 Drawing Sheets

Latin name of the genus and species of the plant claimed: *Euphorbia milii* Desmoul.

Variety denomination: '12-01-ZEU'.

BACKGROUND OF THE INVENTION

The present invention relates to a new and distinct cultivar of *Euphorbia* plant, botanically known as *Euphorbia milii* Desmoul, commonly known by the name of Crown of Thorns, and hereinafter referred to by the name '12-01-ZEU'.

The new *Euphorbia* cultivar is a product of a planned breeding program conducted by the inventor, Steen Thomsen, in Hjortebjergvej, Denmark. The new *Euphorbia* cultivar originated from selection from random crossing of proprietary seedlings of *Euphorbia milii* cultivars. The inventor selected the new *Euphorbia milii* cultivar as a single flowering plant from the progeny of the above polycrosses on the basis of the color of its flowers and leaves.

Asexual reproduction of the new cultivar by terminal cuttings taken and propagated in trial production batches in Hjortebjergvej, Denmark, has demonstrated that the unique features of this new *Euphorbia* cultivar are stable and reproduce true-to-type in many successive generations of asexual reproduction.

BRIEF SUMMARY OF THE INVENTION

The following traits have been repeatedly observed and are determined to be the unique characteristics of '12-01-ZEU'. These characteristics in combination distinguish '12-01-ZEU' as a new and distinct *Euphorbia* cultivar, when grown as described in a 11 cm pot:

1. Plant height of about 20-22 cm and plant width of about 16-18 cm.
2. Grouped disposition of spines.
3. Leaf length about 5-6 cm and the width about 1.5-2 cm.
4. Leaf color on the upper side is RHS Yellow-Green 147A (but darker) and on the underside being RHS Grayed-Purple 187A/187B.
5. The color of the upper side of its big colorful bracts is RHS Red 45D.
6. The size of the bracts are 12-20 mm, and the width are 15-24 mm.
7. Upright to spreading, compact growth habit, with a high number of branches.

Plants of the cultivar '12-01-ZEU' can be compared to plants of the *Euphorbia milii* cultivar 'HJOR 048' (patented, U.S. Plant Pat. No. 17,605) and 'Eros' (patented, U.S. Plant Pat. No. 15,413). In side-by-side comparisons conducted by the inventor in Denmark, plants of the new cultivar '12-01-ZEU' and the comparison cultivars 'HJOR 048' and 'Eros' differ in the following characteristics:

| Trait | '12-01-ZEU' | 'HJOR 048' | 'Eros' |
|---|---|---|---|
| Bract (Flower) color upper side | RHS Red 45D | RHS Red 54A | RHS Red 42B-45C |
| Bract length | 12-20 mm | 8-14 mm | 9 mm |
| Bract width | 15-24 mm | 12-18 mm | 14 mm |

-continued

| Trait | '12-01-ZEU' | 'HJOR 048' | 'Eros' |
|---|---|---|---|
| Leaf color upper side | RHS Yellow-Green 147A (but darker) | RHS Green 137A | RHS Green 139A |
| Leaf color underside | RHS Grayed-Purple 187A/187B | RHS Yellow-Green 144A | RHS Green 139A |
| Leaf size | Leaf length: 5-6 cm<br>Leaf width: 1.5-2.0 cm | Leaf length: 10 cm<br>Leaf width: 4 cm | Leaf length: 7 cm<br>Leaf width: 3 cm |
| Quantity of flowers and buds per plant | 20-30 | 100-120 | — |

BRIEF DESCRIPTION OF THE DRAWINGS

The accompanying color photographs illustrate the overall appearance and details of flower form, color and structures of the new cultivar '12-01-ZEU', showing the colors as true as it is reasonably possible to obtain in color reproductions of this type. Colors in the photographs may differ slightly from the color values cited in the detailed botanical description, which more accurately describe the actual colors of the new *Euphorbia* cultivar. Plants on the pictures are approximately 15 weeks old from sticking, and they are grown in a 11 cm pot.

DETAILED BOTANICAL DESCRIPTION

Figure 1:
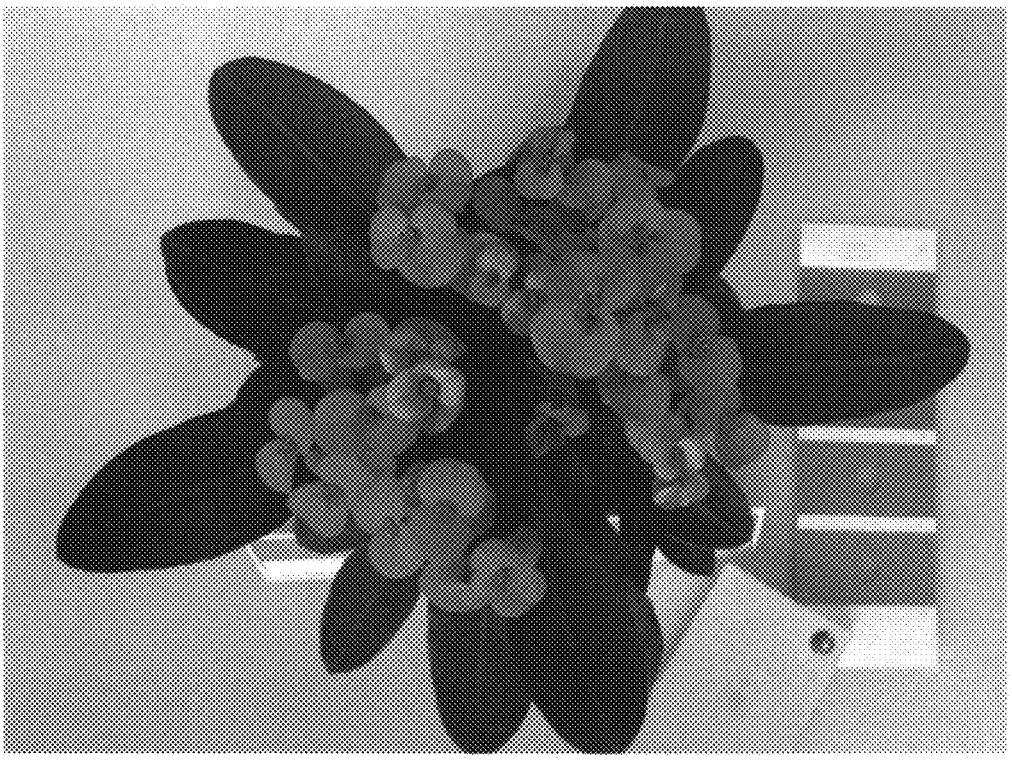
FIG. 1 shows a top view of a typical flowering plant of '12-01-ZEU' as grown in an 11 cm pot.
Figure 2:
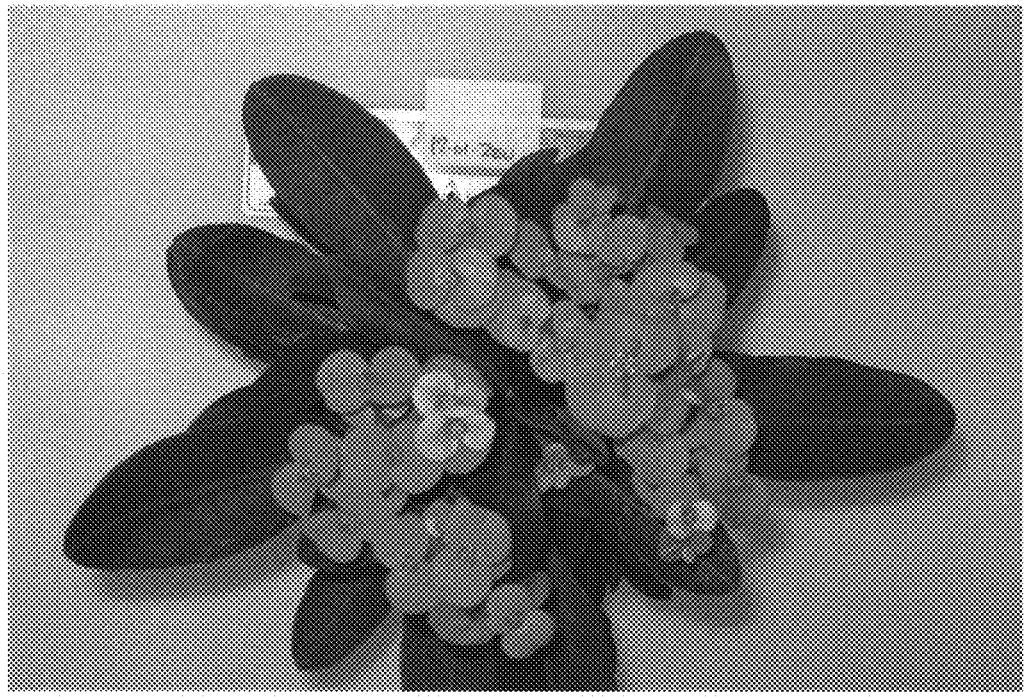
FIG. 2 shows another top view of a typical flowering plant of '12-01-ZEU' as grown in an 11 cm pot (photographed under different light conditions from FIG. 1).
Figure 3:
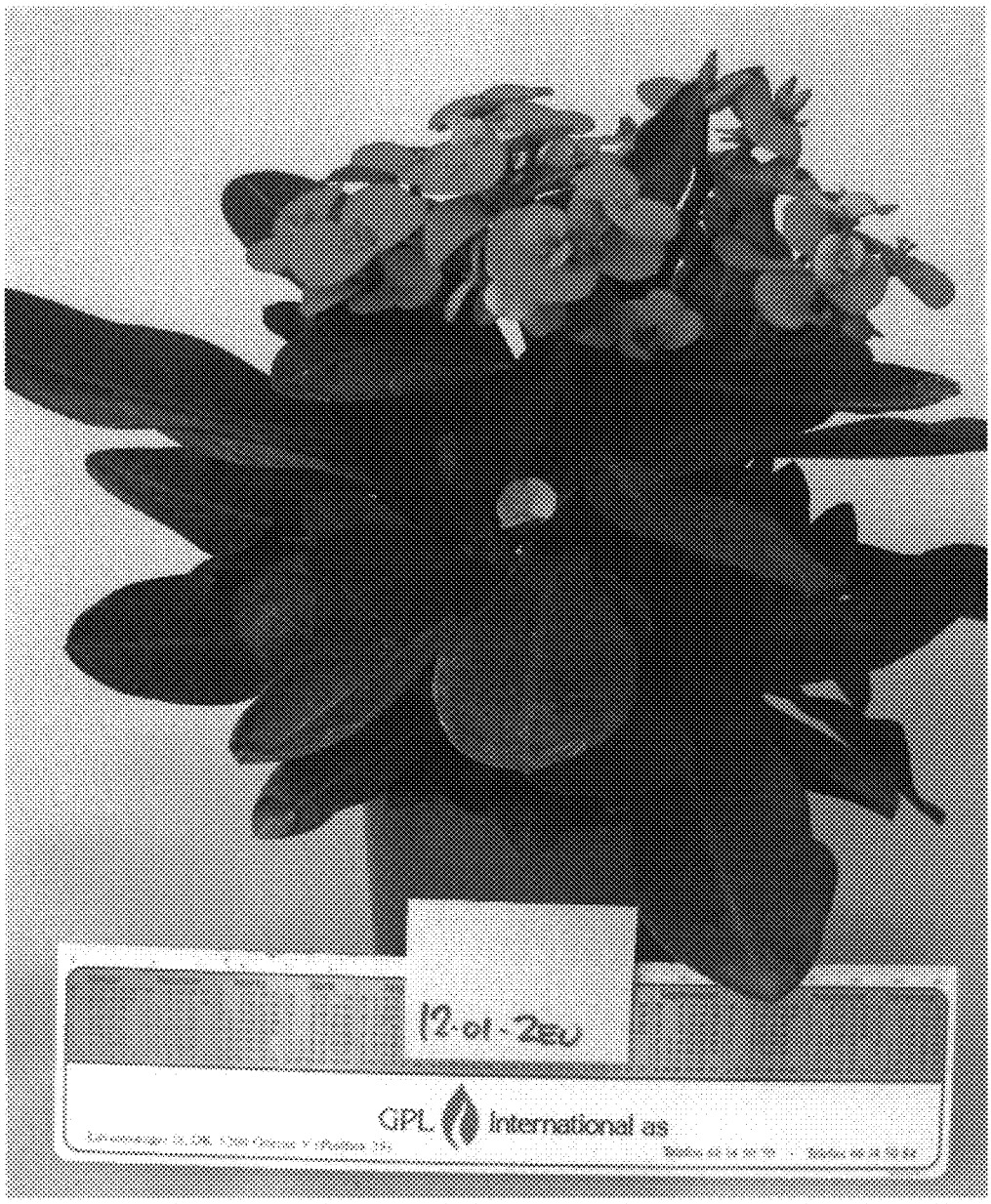
FIG. 3 shows a side view of a typical flowering plant of '12-01-ZEU' as grown in an 11 cm pot.
Figure 4:
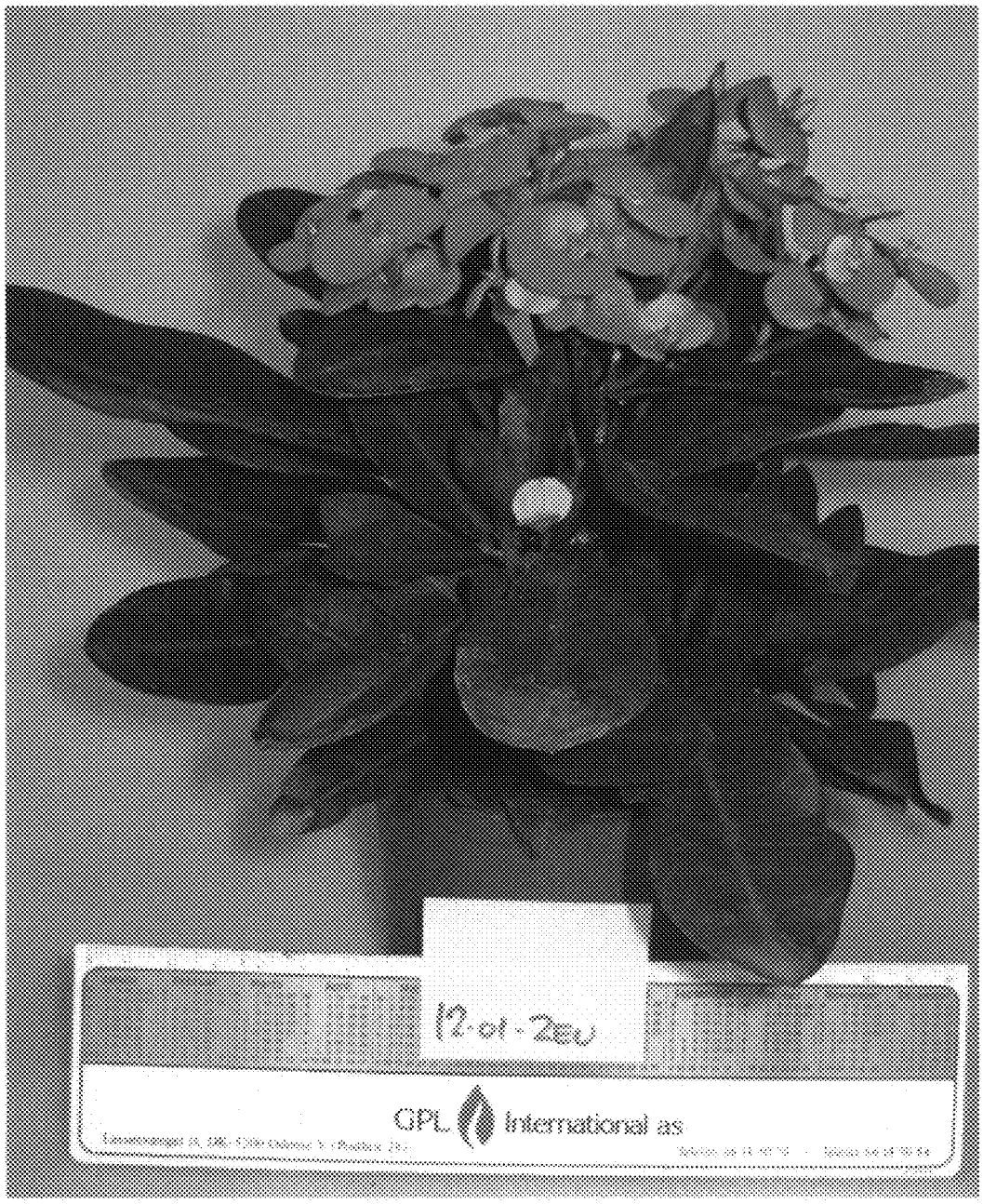
FIG. 4 shows a side view of a typical flowering plant of '12-01-ZEU' as grown in an 11 cm pot (photographed under different light conditions from FIG. 3).
Figure 5:
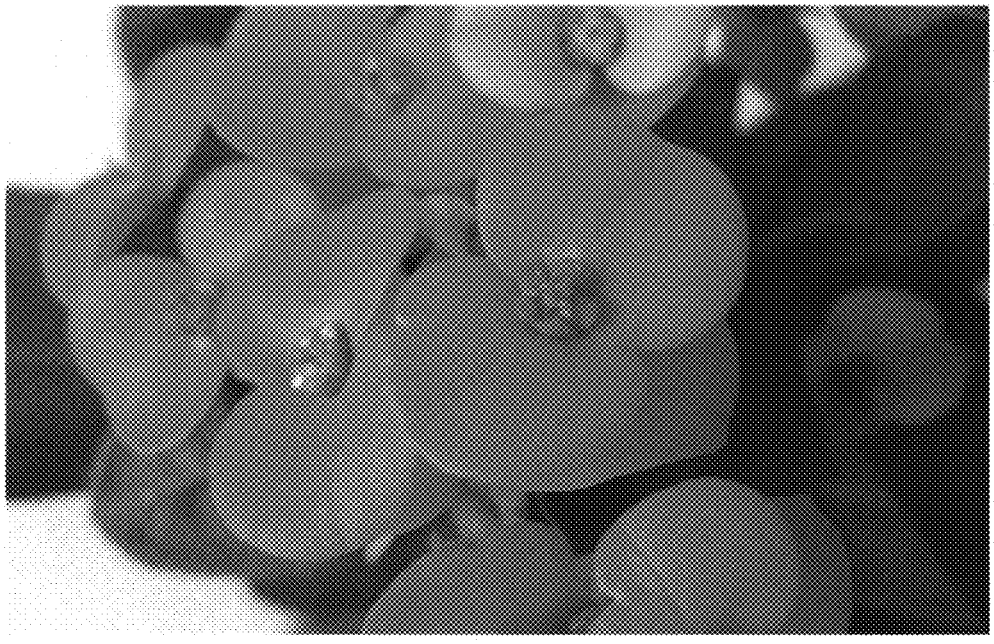
FIG. 5 is a close up of the typical flowers of '12-01-ZEU'.

Plants of the new cultivar '12-01-ZEU' have not been observed under all possible environmental conditions. The phenotype may vary somewhat with variations in the environment such as temperature, light intensity, day length, and fertility level without, however, any variance in genotype.

The aforementioned photographs, together with the following observations, measurements and values describe plants of the new cultivar '12-01-ZEU' as grown in Hjortebjergvej, Denmark, during December-March, under conditions which closely approximate those generally used in commercial practice. Plants of '12-01-ZEU' were grown under the temperature range of about 20-22° C. for a day length of about 12 hours. Artificial light, with an intensity of 50 Watt/m$^2$, was used when the intensity of the day light was less than 40 Watt/m$^2$. Water with an electrical conductivity of about 1.6 ds/m (decisiemens/meter) was used for irrigation. All plants were grown in 11 cm pot in a glass greenhouse. The plants were approximately 15 weeks old when described and measured.

Color observations were taken under natural light, in the month October. Color observations are with reference to The Royal Horticultural Society Colour Chart 2001 (4$^{th}$ edition).

Botanical classification: *Euphorbia milii* Desmoul.

Parentage:

*Female parent*.—Unnamed seedling plant of *Euphorbia*.

*Male parent*.—Unnamed seedling plant of *Euphorbia*.

Propagation:

*Type cutting*.—Terminal vegetative cuttings taken from plants.

*Time to initiate roots*.—About 3 weeks.

Root description:

*Fibrous root color*.—RHS Grayed-Yellow 160B.

Plant description:

General: Succulent well branching shrub, with upright to spreading growth. Stems are thick and have grouped spines, and is containing white sap. High number of leaves per plant, despite the size of plant.

*Form*.—Compact.

*Crop time*.—About 15 weeks.

*Vigor*.—Medium, growing about 1-2 cm per week.

*Plant height*.—About 20-22 cm from soil level to top of plant plane.

*Plant width*.—16-18 cm.

Stem (main center stem):

*Shape*.—Round with 5 rows of prickles along the stem, each with one or more spines.

*Surface*.—Aculeate.

*Diameter*.—1-1.5 cm.

*Length*.—12-16 cm.

*Color of mature stem*.—RHS Grayed-Green 197A/197B.

*Color of immature stem*.—RHS Yellow-Green 148A.

Branches (lateral):

*Branching habit*.—Lateral ascending branches on lower half of the center stem.

*Number of branches per plant*.—10-15.

*Shape*.—Round with 5 rows of prickles along the stem, each with one or more spines. Smaller and thinner than center shoot.

*Surface*.—Aculeate.

*Diameter*.—4-10 mm.

*Length*.—4-7 cm.

*Color of mature stem*.—RHS Grayed-Green 197B.

*Color of immature stem*.—RHS Yellow-Green 148A.

Spines and prickles: High number of spines arising in groups from prickles located in 5 rows along the stems and branches.

*Number of prickle rows along stem*.—5.

*Length of prickle along shoot*.—4-7 mm.

*Number of spines per prickle*.—1-8 (1-3 dominant).

*Length*.—5-12 mm. Longest at the center shoot.

*Thickness of spine near base*.—0.5-2 mm.

*Texture*.—Glabrous.

*Color of prickle and spine inside the plant*.—RHS Grayed-Purple 187A.

*Color of light exposed prickle and spine*.—RHS Grayed-Purple N186B (or darker).

Foliage description:

*Arrangement*.—Leaves alternate, single.

*Number of leaves on central shoot*.—25-30.

*Number of leaves per branch*.—6-14.

*Length*.—5-6 cm.

*Width*.—1.5-2 cm.

*Overall shape of leaf*.—Oblanceolate.

*Shape at apex*.—Obtuse.

*Shape at base*.—Attenuate.

*Margin*.—Entire.

*Texture*.—Glabrate, Glaucescent (thin layer).
*Color of mature leaf upper side*.—RHS Yellow-Green 147A (but darker).
*Color of mature leaf underside*.—RHS Grayed-Purple 187A/187B.
*Color of immature leaf upper side*.—RHS Yellow-Green 146B.
*Color of immature leaf underside*.—RHS Grayed-Purple 177A.
*Venation pattern*.—Venose.
*Venation color upper surface*.—RHS Yellow-Green 146A.
*Venation color lower surface*.—RHS Yellow-Green 145C.
*Petiole length*.—0-10 mm (mostly close to 0 mm).
*Petiole shape*.—Round with flat upper side.
*Petiole diameter*.—2-4 mm.

Flower description:
*Flower arrangement and shape*.—Pseudanthia Flowers. The inflorescence is composed of cymes. Only the nectar glands and the reproductive organs are present. Subtending each cyathium, are two strong colored petal-like bracts. Just above the 2 colored bracts, 2 buds for a second layer of flowers are appearing, forming a new layer of flowers above the old flowers. 2 or more layers is possible.
*Natural flowering season*.—March-September.
*Flower longevity on the plant*.—About 3-4 weeks.
*Quantity of flowers and buds per plant*.—About 20-30.
*Rate of flower opening*.—4-5 per week.
*Fragrance*.—None.

Flower (cyathium):
*Shape*.—Round, upright aspect.
*Height*.—About 5 mm.
*Diameter without bracts*.—About 5 mm.
*Diameter with bracts*.—25-35×15-24 mm.
*Color near upper edge*.—RHS Red 40C.
*Color near base*.—RHS Yellow-Green 145D.

Bracts: The size and color of the bracts, are considered being the main features that gives this plant it's unique ornamental value.
*Number per flower*.—2.
*Arrangement*.—Opposite, sessile, partly overlapping at the base.
*Shape*.—Reniform.
*Base*.—Cordate.
*Apex*.—Rounded.
*Length* (*individual bract*).—12-20 mm.
*Width* (*individual bract*).—15-24 mm.
*Color upper side of immature*.—RHS Red 52A.
*Color underside of immature*.—RHS Red 52B.
*Color upper side of mature*.—RHS Red 45D.
*Color underside of mature*.—RHS Red 50A.
*Margin*.—Entire.
*Texture*.—Glabrous.

Glands: 5 glands.
*Color*.—RHS Yellow-Orange 20A.
*Size*.—1.5×2.5 mm cupulate, containing the nectar.

Peduncles and pedicels:
*Peduncles*.—3-6 cm, slightly sticky.
*Pedicels*.—2-3 cm, slightly sticky.
*Peduncle and pedicels color* (*underneath plant foliage*).—RHS Yellow-Green 145B.
*Peduncle and pedicels color* (*light exposed*).—RHS Gray-Brown 199A (or greener).

Buds:
*Length*.—10-14 mm.
*Shape*.—Acute.
*Color* (*lower half*).—RHS Yellow-Green 145B.
*Color* (*underside of bracts before bending downwards*).—RHS Grayed-Red 178C.

Reproductive organs:

Androecium:
*Stamen number*.—5.
*Stamen length*.—2-3 mm.
*Anther sac*.—2 per filament arranged opposite.
*Anther sac shape*.—Round.
*Anther sac size*.—0.3 mm.
*Anther color*.—RHS Grayed-Purple N187A.
*Filament color*.—Translucent RHS Yellow-Green 145C.
*Pollen color*.—RHS Yellow 11B.

Gynoecium:
*Pistil length*.—6 mm.
*Stigma length*.—1.5 mm.
*Stigma shape*.—5-forked, 1 mm long.
*Stigma color*.—RHS Red 53B.
*Style*.—Length: 1.5 mm.
*Style color*.—RHS Red 53B.
*Ovary length*.—3 mm.
*Ovary diameter*.—1 mm.
*Ovary color*.—RHS Yellow-Green 144B.

Seeds/fruit:
*Number of seeds per fruit*.—3.

Pest/disease tolerance/susceptibility: No specific resistance or susceptibility was observed during cultivation, except some resistance against thrips (*Frankliniella occidentalis*). Plants of the new *Euphorbia milii* '12-01-ZEU' have exhibited good tolerance to drought, rain and wind.

What is claimed is:

1. A new and distinct cultivar of *Euphorbia milii* plant named '12-01-ZEU', as illustrated and described herein.

* * * * *